United States Patent [19]

Panoz

[11] Patent Number: 4,716,040
[45] Date of Patent: Dec. 29, 1987

[54] CONTROLLED ABSORPTION METHYLDOPA PHARMACEUTICAL FORMULATION

[75] Inventor: Donald E. Panoz, Whale Bay, Bermuda

[73] Assignee: Elan Corporation P.L.C., Ireland

[21] Appl. No.: 685,324

[22] Filed: Dec. 20, 1984

[30] Foreign Application Priority Data

Dec. 21, 1983 [IE] Ireland ............... 3026/83

[51] Int. Cl.$^4$ .................. A61K 9/50; A61K 9/58
[52] U.S. Cl. ............................ 424/459; 424/462; 424/468; 424/473; 424/490; 424/497; 514/965
[58] Field of Search ............ 424/19, 20, 22, 468, 424/473, 459, 462, 490, 497; 514/965

[56] References Cited

U.S. PATENT DOCUMENTS

| | | | |
|---|---|---|---|
| 3,965,255 | 6/1976 | Bloch et al. | 424/472 |
| 4,230,687 | 10/1980 | Sair et al. | 514/965 |
| 4,263,273 | 4/1981 | Appelgren et al. | 424/19 |
| 4,361,546 | 11/1982 | Stricker et al. | 424/462 |
| 4,367,217 | 1/1983 | Gruber et al. | 424/19 |
| 4,438,091 | 3/1984 | Gruber et al. | 424/465 |
| 4,499,066 | 2/1985 | Moro et al. | 424/22 |
| 4,555,399 | 11/1985 | Hsiao | 424/80 |
| 4,592,753 | 6/1986 | Panoz | 604/897 |
| 4,600,645 | 7/1986 | Ghebre-Sellassie et al. | 424/19 |
| 4,609,542 | 9/1986 | Panoz et al. | 424/19 |
| 4,610,870 | 9/1986 | Jain et al. | 424/19 |

FOREIGN PATENT DOCUMENTS

| | | |
|---|---|---|
| 0032562 | 7/1981 | European Pat. Off. . |
| 0069259 | 1/1983 | European Pat. Off. . |
| 2116256 | 7/1972 | France . |
| 2039737 | 8/1980 | United Kingdom ......... 424/19 |

Primary Examiner—Ronald W. Griffin
Attorney, Agent, or Firm—Hubbard, Thurman, Turner & Tucker

[57] ABSTRACT

A controlled absorption methyldopa formulation for oral administration comprises a pellet having a core of methyldopa or a pharmaceutically acceptable salt thereof in association with an organic acid, and an outer membrane which permits release of methyldopa in an aqueous medium at a controlled rate which is substantially pH independent. The pellet has a dissolution rate in vitro, which when measured in a Basket Assembly according to U.S. Pharmacopoeia XX at 37° C. and 75 r.p.m., is not more than 50% of the total methyldopa after one hour of measurement. Not more than 80% of the total methyldopa is released after a total of 3 hours of measurement and 100% release is achieved after a total of 7 hours.

11 Claims, 3 Drawing Figures

CONTROLLED ABSORPTION METHYLDOPA PHARMACEUTICAL FORMULATION

BACKGROUND OF THE INVENTION

1. FIELD OF THE INVENTION

This invention relates to a controlled absorption pharmaceutical formulation and, in particular, to a controlled absorption methyldopa formulation.

2. DESCRIPTION OF THE PRIOR ART

Methyldopa (3-hydroxy-α-methyl-L-tyrosine) is an antihypertensive agent which it has been suggested may act centrally by stimulating alpha-adrenergic receptors. It inhibits the decarboxylation of dopa to dopamine and consequently reduces the amount of noradrenaline formed from dopamine. When administered orally the effects of methyldopa may appear after about 2 hours and reach a maximum in 6 to 8 hours, although the maximum hypotensive effect may not occur until the second day of treatment; some effect is still usually apparent 24 hours after a dose. Methyldopa is used in the treatment of moderate to severe hypertension. It acts by reducing the standing blood pressure and also reduces the supine blood pressure.

The usual initial dose by mouth is the equivalent of 250 mg of anhydrous methyldopa twice or thrice daily for two days; this is then adjusted by small increments or decrements not more frequently than every other day according to the response of the patient. The usual maintenance dosage is the equivalent of 0.5 to 2 g of anhydrous methyldopa daily.

A thiazide diuretic is frequently administered simultaneously with methyldopa to combat oedema which is sometimes observed with methyldopa therapy.

Only about one half of an oral dose of methyldopa is absorbed, and peak plasma concentrations occur after about 3 to 6 hours. In persons with normal renal function, 80 or 90% of the drug has been reported to be eliminated from the body in 48 hours. Of the methyldopa eliminated in the urine, about 25% is unchanged and the remainder is as metabolites, mainly a mono-O-sulphate of methyldopa.

It is an object of the present invention to provide a controlled absorption form of methyldopa which is suitable for once daily administration, which is characterised by a high degree of absorption, which is largely invariable from patient to patient, and by significant blood levels of methyldopa which are maintained for an extended period after administration.

SUMMARY OF THE INVENTION

Accordingly, the invention provides a controlled absorption methyldopa formulation for oral administration, comprising a pellet having a core of methyldopa or a pharmaceutically acceptable salt thereof in association with an organic acid, and a multi-layer membrane surrounding said core and containing a major proportion of a pharmaceutically acceptable film forming, water-insoluble polymer and a minor proportion of a pharmaceutically acceptable film forming, water-soluble polymer, the number of layers in said membrane and the ratio of said water-soluble polymer to said water-insoluble polymer being effective to permit release of said methyldopa from said pellet at a rate allowing controlled absorption thereof over a twenty four hour period following oral administration said rate being measured in vitro as a dissolution rate which is substantially pH independent and which when measured in a Basket Assembly according to U.S. Pharmacopoeia XX at 37° C. and 75 r.p.m. substantially corresponds to the following dissolution pattern:

(a) from 25 and 50% of the total methyldopa is released after 1 hour of measurement in said assembly;

(b) from 50 to 80% of the total methyldopa is released after 3 hours of measurement in said assembly;

(c) from 80 to 100% of the total methyldopa is released after 5 hours of measurement in said assembly; and (d) from 90 to 100% of the total methyldopa is released after 7 hours of measurement in said assembly.

DESCRIPTION OF THE PREFERRED EMBODIMENTS

Preferably, the organic acid is represented by one or more of the following acids: adipic acid, citric acid, fumaric acid, malic acid, succinic acid and tartaric acid.

The methyldopa and organic acid are preferably present in a ratio of from 1:1 to 10:1.

Preferably the core comprises methyldopa or a pharmaceutically acceptable salt thereof and the associated organic acid embedded in a polymeric material in a multilayer arrangement. The polymeric material in which the methyldopa is embedded may be rapidly soluble in water or, alternatively, be readily permeable to methyldopa and water.

The term water-soluble polymer as used herein includes polymers which are freely permeable to water such as Eudragit RL. Likewise, the term water-insoluble polymer as used herein includes polymers which are slightly permeable to water such as Eudragit RS.

The polymeric material may consist solely of a water soluble polymer or, alternatively, it may include a minor proportion of a water insoluble polymer. The ratio of water soluble to water insoluble polymer is determined by the particular combination of polymers selected.

The water soluble polymer is suitably hydroxypropylmethylcellulose, polyvinylpyrrolidone or a polymer sold under the Trade Mark Eudragit RL.

The water insoluble polymer is suitably a cellulose ether such as methyl-, ethyl- or propylcellulose, Shellac or a polymer sold under the Trade Mark Eudragit RS.

The core suitably has between 20 and 120 layers and is built up in a manner known per se.

Further, preferably, the multi-layer arrangement of methyldopa, organic acid and polymeric material is built up on a central inert core suitably consisting of a non-pareil seed of sugar or starch having an average diameter in the range 0.3–0.7 mm, especially 0.4–0.5 mm, in a conventional coating pan.

The core may also include other components such as a lubricant, a dispersing agent or a surfactant. A suitable lubricant is talc and a suitable surfactant is sodium lauryl sulphate.

In a preferred embodiment, the core comprises: (a) a powder mixture comprising methyldopa or a pharmaceutically acceptable salt thereof and at least one organic acid selected from the group consisting of adipic acid, citric acid, fumaric acid, malic acid, succinic acid and tartaric acid, and (b) a polymeric material comprising a major proportion of a pharmaceutically acceptable water-soluble polymer and a minor proportion of a pharmaceutically acceptable water-insoluble polymer, and the core comprises layers of the powder mixture and the polymeric material superimposed one upon the other wherein the polymeric material is present in an amount of sufficient to ensure that all of the powder mixture is coated into the core.

The methyldopa, organic acid and optionally other components such as a lubricant are blended to form a homogeneous powder. Alternate layers of a coating solution of the polymeric material and the powder are applied to the central inert core so as to build up the multi-layer arrangement of the active core. The concentration of the polymeric material in the coating solution is determined by the viscosity of the final solution. Especially preferred coating solutions include:

(a) 5%–10% Polyvinylpyrrolidone in isopropanol.
(b) 5% Hydroxypropylmethylcellulose in methanol/methylene chloride 50/50.
(c) 5% Eudragit RL in isopropanol/acetone 60/40.

The multi-layer membrane preferably has a major proportion of a water insoluble polymer and a minor proportion of a water soluble polymer, the ratio of water insoluble to water soluble polymer being determined by the inherent solubility characteristics of the polymers selected.

Suitable combinations of water insoluble and water soluble polymers for the outer membrane include: Shellac and polyvinylpyrrolidone in a ratio of 4:1 to 19:1; ethylcellulose and hydroxypropylcellulose in a ratio of 3:1 to 19:1; and Eudragit RS and Eudragit RL in a ratio of 3:1 to 9:1.

Polymers sold under the Trademark Eudragit RL and RS are resins comprising copolymers of acrylic and methacrylic acid esters with a low content of quaternary ammonium groups and are described in the "Eudragit" brochure of Rohm Pharma GmbH (1982) wherein detailed physical-chemical data of the products is given. The ammonium groups are present as salts and gives rise to permeability of the lacquer films. Eudragit RL and RS are freely permeable (RL) or slightly permeable (RS), respectively independent of pH.

The multi-layer membrance may also be composed of a major proportion of a non-porous polymer and a minor proportion of a porous polymer, the ratio of non-porous to porous polymer being determined by the inherent porosity of the respective polymers.

The multi-layer membrane is built up by applying a plurality of coats of membrane polymer solution to the core as hereinafter described. The membrane solution contains the polymers dissolved in a suitable solvent, optionally in the presence of a lubricant. Suitable lubricants are talc, stearic acid and magnesium stearate. Preferably, the number of coats of membrane solution applied is between 8 and 30 coats. Preferably 2–25 ml of membrane solution is applied per kilogram of cores.

Especially preferred membrane solutions include:

| | |
|---|---|
| (a) 7.5% Polyvinylpyrrolidone in isopropanol. | 5–20 Parts by volume |
| 17.5% Shellac in ethanol | 80–95 Parts by volume |
| Talc (lubricant) | 100 Parts by weight |
| (b) 5% Hydroxypropylmethylcellulose in methanol/methylene chloride 50/50. | 5–25 Parts by volume |
| 5% Ethylcellulose in methanol/methylene chloride 50/50. | 75–95 Parts by volume |
| Diethylphthalate (plasticiser). | 0.5 Parts by weight |
| Talc (lubricant). | 100 Parts by weight |
| (c) 5% Eudragit RL in isopropanol/acetone 60/40. | 10–25 Parts by volume |
| 5% Eudragit RS in isopropanol/acetone 60/40. | 75–90 Parts by volume |
| Magnesium stearate (lubricant). | 25 Parts by weight |

The pellets may be filled into hard gelatine capsules.

The invention will be further illustrated by the following Examples.

EXAMPLE 1

Methyldopa (4 kg), anhydrous citric acid (0.6 kg), fumaric acid (0.4 kg) and sodium lauryl sulphate (0.08 kg) were blended and passed through a No. 100 mesh screen. The milled mixture was wetted in a Z blade mixer with isopropanol (1 litre) in order to disperse the sodium lauryl sulphate more completely. The mixture was dried at 45° C. for 12 hours and again milled through a No. 100 mesh screen. The mixture was treated in a ball mill in order to further reduce the particle size.

Starch/sugar seeds (0.4 to 0.5 mm diameter) (0.5 kg) were rotated in a standard coating pan. The fine powder mixture was applied to the seeds using 7.5% (w/v) polyvinylpyrrolidone in isopropanol as the coating solution. The seeds were coated with a measured volume of coating solution followed by dusting on of a measured weight of the powder mix. The coated seeds were allowed to dry and the coating step repeated until all of the powder had been applied. The coated seeds were then dried at 45° C. overnight to remove all traces of solvent.

The coated seeds defining the active core of the pellet according to the invention were then surrounded by an outer membrane by applying 11 coats of a solution consisting of:

| | |
|---|---|
| 15% Polyvinylpyrrolidone in isopropanol | 1 Part by volume |
| Isopropanol | 5 Parts by volume |
| 35% Shellac in ethanol | 4 Parts by volume |
| Talc | 5 Parts by weight. |

The membrane solution was applied to the coated seeds as "coats" in the coating pan to form pellets, each coat being 5 ml of solution per kg of coated seeds. After each coat had been applied the pellets were air dried in the coating pan.

The finished pellets were then subjected to a dissolution test. Prior to performing the dissolution test the pellets were dried at 45° C. to evaporate all of the solvent.

The dissolution rate of the pellets was tested by the method of U.S. Pharmacopoeia XX (Basket Method) in buffered media at pH 3.0, pH 6.0 and pH 7.5. The dissolution rate, which was found to be substantially pH independent, was as follows:

| Time (h) | % release pH 3.0 | % release pH 6.0 | % release pH 7.5 |
|---|---|---|---|
| 1 | 38.2 | 37.1 | 39.2 |
| 3 | 69.5 | 66.7 | 69.1 |
| 5 | 85.4 | 81.6 | 84.4 |
| 7 | 93.8 | 90.6 | 93.6 |

EXAMPLE 2

Methyldopa (4 kg), tartaric acid (0.6 kg), succinic acid (0.4 kg) and talc (0.5 kg) were blended and milled through a No. 100 mesh screen. The milled blend was applied onto starch/sugar seeds (0.4–0.5 mm diameter) (1 kg) using 5% hydroxypropylmethylcellulose in methanol/methylene chloride-50/50 as the coating solution, following the procedure described in Example 1.

The coated seeds were then surrounded by a membrane by applying 10 coats of a solution consisting of:

| | |
|---|---|
| 5% Hydroxypropylmethylcellulose in methanol/methylene chloride 50/50. | 1 Part by volume |
| 5% Ethylcellulose in methanol/methylene chloride 50/50. | 9 Parts by volume |
| Methanol/methylene chloride 50/50 | 10 Parts by volume |
| Stearic acid | 10 Parts by weight |

The membrane was applied following the procedure according to Example 1.

The dissolution rate of the pellets, which was measured according to the procedure followed in Example 1, was:

| Time (h) | % release pH 3.0 | % release pH 6.0 | % release pH 7.5 |
|---|---|---|---|
| 1 | 36.8 | 34.2 | 31.7 |
| 3 | 75.3 | 76.1 | 72.2 |
| 5 | 86.9 | 82.2 | 81.2 |
| 7 | 96.3 | 92.3 | 91.2 |

EXAMPLE 3

Methyldopa (4 kg), tartaric acid (0.3 kg), citric acid (0.3 kg), adipic acid (0.3 kg) and sodium lauryl sulphate (0.1 kg) were blended and milled through a No. 100 mesh screen. The blend was applied onto starch/sugar seeds (0.4–0.5 mm in diameter) (0.75 kg) using 5% Eudragit RL in acetone/isopropanol-40:60 as the coating solution, following the procedure of Example 1. The coated seeds were dried at 45° C. and then a membrane was applied thereto, following the procedure of Example 1, by applying 40 coats of a solution consisting of:

| | |
|---|---|
| 5% Eudragit RL in acetone/isopropanol 40/60. | 15 Parts by volume |
| 5% Eudragit RS in acetone/isopropanol 40/60. | 85 Parts by volume |

The dissolution rate of the pellets was determined following the procedure of Example 1 and was found to be as follows:

| Time (h) | % release pH 3.0 | % release pH 6.0 | % release pH 7.5 |
|---|---|---|---|
| 1 | 36.0 | 39.1 | 37.2 |
| 3 | 75.1 | 73.1 | 71.1 |
| 5 | 88.3 | 87.2 | 86.4 |
| 7 | 100 | 92.4 | 94.0 |

EXAMPLE 4

Pellets prepared according to Example 1 were filled directly into hard gelatine capsules without the addition of any extra ingredients so as to obtain capsules containing 350 mg and 700 mg methyldopa, respectively.

Bioavailability Data

TABLE 1

Figure 1:
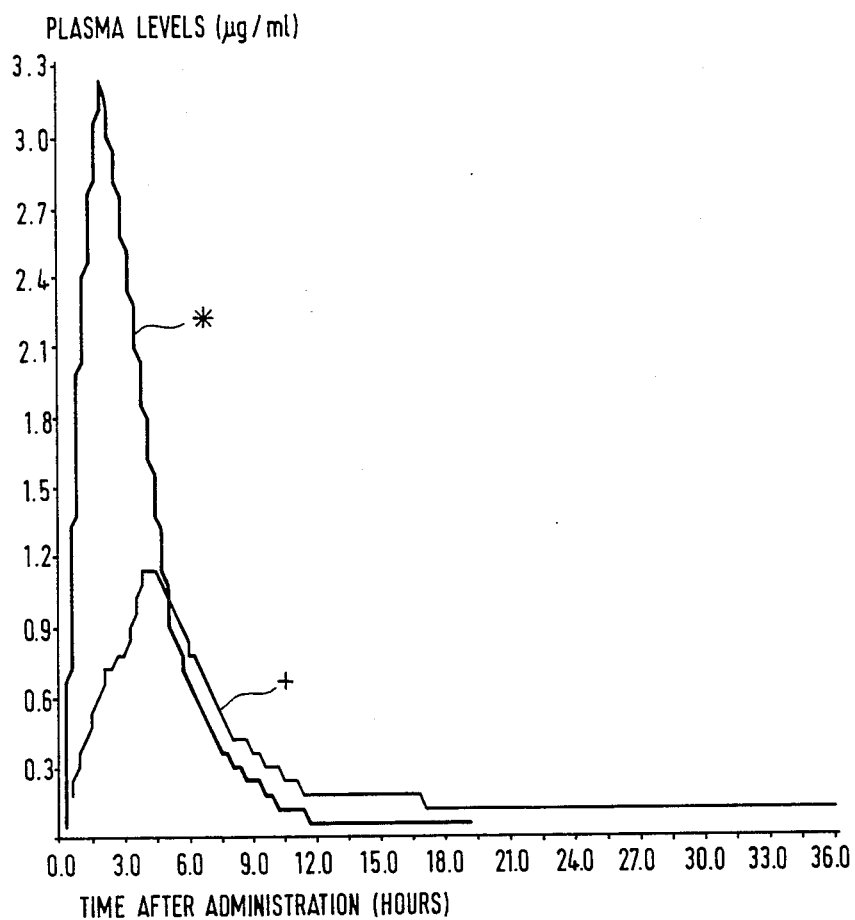
FIG. 1 is a graph of plasma levels ($\mu$g/ml) versus time after administration (hours) for a single dose (750 mg) of methyldopa in capsule form according to Example 4 (+) compared with a single dose (750 mg) of Aldomet (Aldomet is a Trade Mark) tablets (*). The graphs of FIG. 1 were drawn from the mean values obtained for six subjects according to the data listed in Table 1.
Figure 2:
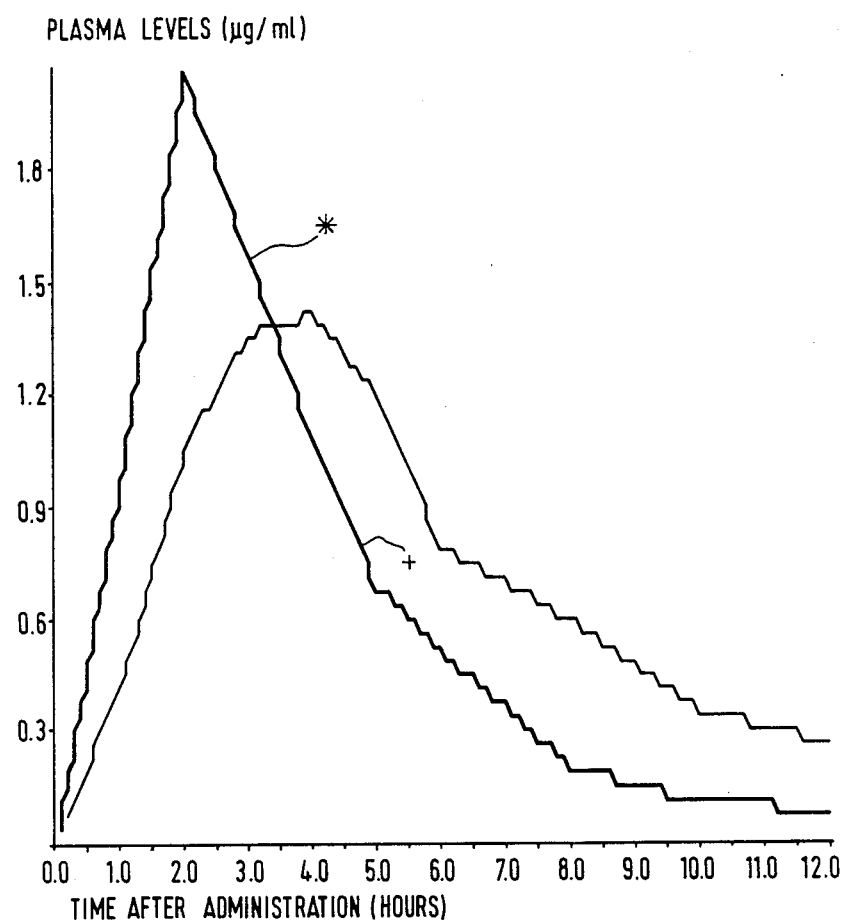
FIG. 2 is a graph of plasma levels ($\mu$g/ml) versus time after administration (hours) for a single dose (750 mg) of methyldopa in capsule form prepared from pellets according to Example 2 (+) compared with a single dose (750 mg) of Aldomet Tables (*). The graphs of FIG. 2 were drawn from the mean values obtained for six subjects according to the data listed in Table 2.
Figure 3:
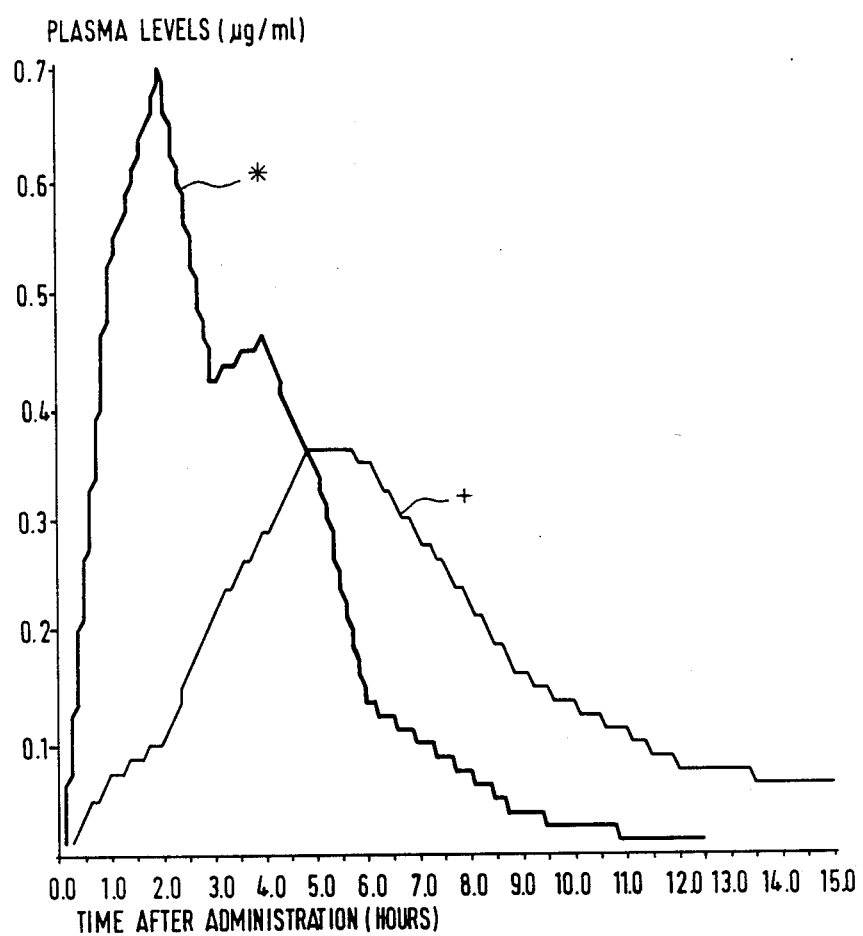
FIG. 3 is a graph of plasma levels ($\mu$g/ml) versus time after administration (hours) for a single dose (250 mg) of methyldopa in capsule form prepared from pellets according to Example 3 (+) compared with a single dose (250 mg) of Aldomet tablets (*). The graphs of FIG. 3 were drawn from the mean values obtained for four subjects according to the data listed in Table 3.

| SUBJ | HOURS AFTER ADMINISTRATION | | | | | | | | | | | | | AUC* |
|---|---|---|---|---|---|---|---|---|---|---|---|---|---|---|
| | 0.00 | 1.00 | 2.00 | 3.00 | 4.00 | 5.00 | 6.00 | 7.00 | 8.00 | 10.00 | 12.00 | 24.00 | 36.00 | |
| METHYLDOPA - per Example 4 750 mg single dose study Plasma Levels ($\mu$g/ml) | | | | | | | | | | | | | | |
| 1 | 0.00 | 0.34 | 0.84 | 0.98 | 1.10 | 1.16 | 1.09 | 0.84 | 0.68 | 0.36 | 0.27 | 0.11 | 0.10 | 11.90 |
| 2 | 0.00 | 0.40 | 0.75 | 0.69 | 0.61 | 0.51 | 0.27 | 0.19 | 0.14 | 0.10 | 0.07 | 0.08 | 0.07 | 5.70 |
| 3 | 0.00 | 0.13 | 0.28 | 0.54 | 0.90 | 1.27 | 0.83 | 0.58 | 0.38 | 0.25 | 0.17 | 0.13 | 0.10 | 8.95 |
| 4 | 0.00 | 0.46 | 0.48 | 0.73 | 2.10 | 1.20 | 1.00 | 0.80 | 0.35 | 0.37 | 0.16 | 0.15 | 0.10 | 11.47 |
| 5 | 0.00 | 0.14 | 0.52 | 0.79 | 1.63 | 1.61 | 1.14 | 1.08 | 0.90 | 0.42 | 0.19 | 0.12 | 0.10 | 12.47 |
| 6 | 0.00 | 0.78 | 1.29 | 1.13 | 0.91 | 0.70 | 0.52 | 0.34 | 0.25 | 0.25 | 0.17 | 0.13 | 0.10 | 9.90 |
| MEAN | 0.00 | 0.38 | 0.69 | 0.81 | 1.19 | 1.08 | 0.81 | 0.64 | 0.45 | 0.29 | 0.17 | 0.12 | 0.10 | 10.06 |
| ST DEV | 0.00 | 0.24 | 0.35 | 0.21 | 0.52 | 0.40 | 0.35 | 0.33 | 0.29 | 0.12 | 0.06 | 0.02 | 0.01 | 2.51 |
| CV (%) | 0.00 | 64.04 | 51.08 | 26.21 | 43.91 | 37.37 | 42.84 | 52.21 | 63.35 | 39.83 | 37.28 | 19.71 | 12.89 | 24.92 |
| METHYLDOPA - Aldomet 750 mg single dose study Plasma levels ($\mu$g/ml) | | | | | | | | | | | | | | |
| 1 | 0.00 | 5.33 | 4.58 | 3.43 | 1.50 | 0.90 | 0.39 | 0.34 | 0.19 | 0.04 | 0.05 | 0.00 | 0.00 | 17.18 |
| 2 | 0.00 | 0.43 | 3.19 | 2.41 | 1.88 | 0.98 | 0.42 | 0.39 | 0.24 | 0.13 | 0.00 | 0.00 | 0.00 | 10.32 |
| 3 | 0.00 | 1.27 | 2.35 | 1.89 | 1.21 | 0.62 | 0.58 | 0.28 | 0.21 | 0.10 | 0.00 | 0.00 | 0.00 | 8.72 |
| 4 | 0.00 | 2.90 | 3.16 | 2.24 | 2.14 | 1.03 | 0.83 | 0.37 | 0.34 | 0.16 | 0.10 | 0.00 | 0.00 | 14.20 |
| 5 | 0.00 | 2.45 | 3.11 | 1.90 | 1.59 | 1.04 | 0.96 | 0.93 | 0.90 | 0.39 | 0.26 | 0.00 | 0.00 | 15.93 |
| 6 | 0.00 | 0.88 | 3.41 | 3.67 | 2.18 | 1.16 | 0.74 | 0.31 | 0.06 | 0.10 | 0.06 | 0.00 | 0.00 | 13.06 |

TABLE 1-continued

| SUBJ | _____ HOURS AFTER ADMINISTRATION _____ | | | | | | | | | | | | | AUC* |
|---|---|---|---|---|---|---|---|---|---|---|---|---|---|---|
| | 0.00 | 1.00 | 2.00 | 3.00 | 4.00 | 5.00 | 6.00 | 7.00 | 8.00 | 10.00 | 12.00 | 24.00 | 36.00 | |
| MEAN | 0.00 | 2.21 | 3.30 | 2.59 | 1.75 | 0.96 | 0.65 | 0.44 | 0.32 | 0.15 | 0.08 | 0.00 | 0.00 | 13.23 |
| ST DEV | 0.00 | 1.79 | 0.72 | 0.77 | 0.38 | 0.18 | 0.23 | 0.24 | 0.30 | 0.12 | 0.10 | 0.00 | 0.00 | 3.25 |
| CV (%) | 0.00 | 81.17 | 21.94 | 29.87 | 21.89 | 19.35 | 35.03 | 56.09 | 91.72 | 79.95 | 123.62 | 0.00 | 0.00 | 24.54 |

*Area under the curve
**Coefficient of variation

TABLE 2

| SUBJ | _____ HOURS AFTER ADMINISTRATION _____ | | | | | | | | | | AUC* |
|---|---|---|---|---|---|---|---|---|---|---|---|
| | 0.00 | 1.00 | 2.00 | 3.00 | 4.00 | 5.00 | 6.00 | 8.00 | 10.00 | 12.00 | |
| METHYLDOPA - per Example 2 750 mg single dose study Plasma Levels (μg/ml) | | | | | | | | | | | |
| 1 | 0.00 | 0.77 | 1.75 | 2.26 | 2.86 | 2.10 | 1.40 | 1.17 | 0.68 | 0.55 | 16.09 |
| 2 | 0.00 | 0.41 | 1.27 | 0.98 | 0.91 | 0.85 | 0.52 | 0.35 | 0.28 | 0.10 | 6.56 |
| 3 | 0.00 | 0.10 | 0.15 | 0.45 | 0.70 | 1.10 | 0.88 | 0.65 | 0.35 | 0.20 | 6.02 |
| 4 | 0.00 | 0.32 | 0.55 | 0.87 | 1.13 | 1.10 | 0.85 | 0.60 | 0.24 | 0.26 | 7.19 |
| 5 | 0.00 | 0.65 | 1.01 | 0.80 | 0.89 | 0.70 | 0.47 | 0.32 | 0.32 | 0.27 | 6.31 |
| 6 | 0.00 | 0.20 | 1.60 | 2.80 | 2.00 | 1.40 | 0.65 | 0.50 | 0.25 | 0.18 | 10.66 |
| MEAN | 0.00 | 0.41 | 1.06 | 1.36 | 1.42 | 1.21 | 0.80 | 0.60 | 0.35 | 0.26 | 8.80 |
| ST DEV | 0.00 | 0.26 | 0.62 | 0.94 | 0.84 | 0.50 | 0.34 | 0.31 | 0.17 | 0.15 | 3.95 |
| CV (%) | 0.00 | 63.44 | 58.47 | 69.05 | 59.58 | 41.25 | 42.79 | 51.69 | 46.80 | 59.53 | 44.92 |
| METHYLDOPA - Aldomet (Merck) 750 mg single dose study Plasma levels (μg/ml) | | | | | | | | | | | |
| 1 | 0.00 | 2.50 | 4.01 | 2.62 | 1.63 | 1.09 | 0.66 | 0.17 | 0.25 | 0.21 | 13.89 |
| 2 | 0.00 | 1.14 | 3.21 | 2.73 | 2.23 | 0.88 | 1.10 | 0.45 | 0.29 | 0.20 | 13.52 |
| 3 | 0.00 | 1.01 | 1.67 | 0.87 | 0.79 | 0.58 | 0.27 | 0.27 | 0.07 | 0.03 | 6.04 |
| 4 | 0.00 | 0.00 | 0.77 | 0.59 | 0.73 | 0.68 | 0.39 | 0.25 | 0.01 | 0.08 | 3.96 |
| 5 | 0.00 | 0.42 | 1.80 | 1.43 | 0.74 | 0.68 | 0.52 | 0.06 | 0.00 | 0.00 | 5.97 |
| 6 | 0.00 | 0.80 | 0.91 | 1.16 | 0.38 | 0.24 | 0.15 | 0.00 | 0.00 | 0.00 | 3.72 |
| MEAN | 0.00 | 0.98 | 2.06 | 1.57 | 1.08 | 0.69 | 0.52 | 0.20 | 0.10 | 0.09 | 7.85 |
| ST DEV | 0.00 | 0.85 | 1.29 | 0.90 | 0.70 | 0.29 | 0.34 | 0.16 | 0.13 | 0.10 | 4.64 |
| CV (%) | 0.00 | 87.25 | 62.61 | 57.70 | 64.45 | 41.45 | 65.68 | 80.75 | 128.04 | 111.07 | 59.15 |

*Area under the curve
**Coefficient of variation

TABLE 3

| SUBJ | _____ HOURS AFTER ADMINISTRATION _____ | | | | | | | | | | AUC* |
|---|---|---|---|---|---|---|---|---|---|---|---|
| | 0.00 | 1.00 | 2.00 | 3.00 | 4.00 | 5.00 | 6.00 | 9.00 | 12.00 | 15.00 | |
| METHYLDOPA - Aldomet . . . 250 mg . . . Plasma Levels (μg/ml) | | | | | | | | | | | |
| 1 | 0.00 | 0.16 | 0.73 | 0.67 | 0.99 | 0.76 | 0.14 | 0.01 | 0.00 | 0.00 | 3.62 |
| 2 | 0.00 | 0.74 | 0.96 | 0.52 | 0.44 | 0.32 | 0.18 | 0.07 | 0.03 | 0.00 | 3.64 |
| 3 | 0.00 | 0.81 | 0.51 | 0.24 | 0.14 | 0.09 | 0.06 | 0.03 | 0.00 | 0.00 | 2.00 |
| 4 | 0.00 | 0.38 | 0.60 | 0.26 | 0.27 | 0.22 | 0.17 | 0.03 | 0.00 | 0.00 | 2.16 |
| MEAN | 0.00 | 0.52 | 0.70 | 0.42 | 0.46 | 0.35 | 0.14 | 0.04 | 0.01 | 0.00 | 2.86 |
| ST DEV | 0.00 | 0.31 | 0.20 | 0.21 | 0.37 | 0.29 | 0.05 | 0.03 | 0.02 | 0.00 | 0.90 |
| *CV (%) | 0.00 | 58.64 | 27.92 | 49.36 | 81.32 | 83.65 | 39.56 | 71.90 | 200.00 | 0.00 | 31.43 |
| MEHTYLDOPA . . . per Example 3 . . . 250 mg . . . Plasma levels (μg/ml) | | | | | | | | | | | |
| 1 | 0.00 | 0.02 | 0.08 | 0.29 | 0.27 | 0.34 | 0.50 | 0.24 | 0.11 | 0.07 | 3.16 |
| 2 | 0.00 | 0.06 | 0.10 | 0.27 | 0.22 | 0.27 | 0.25 | 0.10 | 0.05 | 0.03 | 1.92 |
| 3 | 0.00 | 0.10 | 0.11 | 0.09 | 0.22 | 0.25 | 0.25 | 0.11 | 0.06 | 0.04 | 1.84 |
| 4 | 0.00 | 0.10 | 0.12 | 0.22 | 0.42 | 0.61 | 0.41 | 0.19 | 0.10 | 0.09 | 3.30 |
| MEAN | 0.00 | 0.07 | 0.10 | 0.22 | 0.28 | 0.37 | 0.35 | 0.16 | 0.08 | 0.06 | 2.55 |
| ST DEV | 0.00 | 0.04 | 0.02 | 0.09 | 0.09 | 0.17 | 0.12 | 0.07 | 0.03 | 0.03 | 0.78 |
| CV (%) | 0.00 | 54.71 | 16.66 | 41.36 | 33.50 | 45.23 | 35.16 | 41.77 | 36.80 | 47.89 | 30.60 |

*Area under the curve
**Coefficient of variation

CLINICAL EVALUATION

In vivo studies carried out in humans with methyldopa capsules prepared in Example 4 have shown that the pellets according to the invention have a prolonged absorption pattern and a consistency of absorption which is not obtained with conventional oral methyldopa preparations. On the basis of these in vivo studies it was anticipated that methyldopa capsules prepared according to Example 4, dose for dose, should exert a greater antihypertensive effect than Aldomet. Thus a therapeutically equivalent dosage of a methyldopa formulation according to the invention should contain a lower amount of active ingredient. Therefore, to test this hypothesis, in the first of five clinical trials described below the antihypertensive activity of methyldopa capsules prepared in Example 4 administered as 350 mg (low-dose) and 700 mg (high-dose) once-daily was compared with and found to be equivalent to Aldomet 500 mg (low-dose) and 1000 mg (high-dose) in 12-hourly divided doses. These doses of methyldopa were then maintained throughout the other clinical trials in which the antihypertensive activity of capsules prepared in Example 4 was compared with other standard antihypertensive treatments, namely a diuretic, a beta-adrenergic blocker and a diuretic/beta-adrenergic blocker combination.

The five clinical trials were carried out to determine the antihypertensive activity of a methyldopa formulation according to the invention and to compare these effects with those of standard antihypertensive agents in the control of mild to moderate hypertension.

The five clinical trials were:
1. A double blind randomized crossover study comparing capsules prepared in Example 4, administered once daily, with Aldomet administered twice daily. A total of 26 patients were admitted to this trial.
2. A single blind randomized parallel group study comparing capsules prepared in Example 4, administered once daily, with Chlorthalidone (diuretic), administered once daily. A total of 30 patients (15 per group) were admitted to this trial.
3. A single blind randomized parallel group study comparing capsules prepared in Example 4, administered once daily, with Atenolol (beta-adrenergic blocker), administered once daily. A total of 30 patients (15 per group) were admitted to this trial.
4. A single blind randomized parallel group study comparing capsules prepared in Example 4, administered once daily, with Chlorthalidone, administered once daily. A total of 24 patients (14 capsules of Example 4; 10 Chlorthalidone) were admitted to this trial.
5. A non-comparative study monitoring the efficacy and tolerability of capsules prepared in Example 4, administered once daily. A total of 20 patients were admitted to this trial.

The features common to all trials were:
(a) All trials were carried out in patients suffering from mild to moderate essential hypertension (diastolic B.P. between 95 and 114 mm Hg; systolic B.P. between 150 and 190 mm Hg) Class I, II WHO.
(b) All blood pressure measurements were made immediately prior to dosing.
(c) A baseline washout period, providing a measure of the level of uncontrolled blood pressure.
(d) A dose-adjustment step so that those patients failing to be controlled on a "low dose" schedule (350 mg capsules of Example 4; 500 mg Aldomet; 25 mg Chlorthalidone; 100 mg Atenolol) were advanced to a "high dose" schedule (capsules of Example 4 700 mg; Aldomet 1000 mg; Chlorthalidone 50 mg; Atenolol 100 mg + Chlorthalidone 100 mg).
(e) An objective measure of treatment failure by defining an end-of-treatment supine diastolic blood pressure of greater than 95 mm Hg, as indicating lack of blood pressure control.

Features (a)–(e) common to all of the five trials may be used to summarize the combined results of the trials.
1. The average results of supine blood pressure for the 130 patients who entered into the trials are given in the following Table 4.

TABLE 1

| Group | Average Blood Pressure (mm Hg) | |
|---|---|---|
| | Systolic | Diastolic |
| Baseline | 174.3 | 107.0 |
| Treatment with methyldopa capsules of Example 4 | 151.7 | 90.4 |
| Standard treatment | 152.7 | 91.2 |

Thus it is apparent that the methyldopa formulation according to the invention is as effective an antihypertensive agent in mild to moderate hypertension, as standard treatment. In addition, in each of the individual comparative studies, treatment with methyldopa capsules according to Example 4 was observed to be equivalent in terms of its antihypertensive activity with the alternative treatments.

2. If the combined results of the four comparative trials are analysed for the frequency of low-dose treatment versus high-dose treatment, the following pattern emerges:

| | Methyldopa Capsules of Example 4 | Standard |
|---|---|---|
| Low-dose | 34 | 20 |
| High-dose | 23 | 53 |

When analysed statistically using a Chi-squared test (two-tailed), the standard treatments showed a significantly higher ($p < 0.05$) incidence of being advanced to a high-dosage regimen. This indicates a greater consistency with the methylpoda according to the invention as opposed to other standard treatments.

3. If the combined results of the four comparative trials are analysed for the frequency of treatment failure (supine diastolic B.P. > 95 mm Hg) then the following pattern emerges:

| | Methyldopa according to Example 4 | Standard |
|---|---|---|
| Controlled | 58 | 45 |
| Not-controlled | 12 | 21 |

When analysed statistically using a Chi-squared test (two-tailed), the standard treatments showed a significantly higher ($p < 0.05$) incidence of treatment failure, again indicating the superiority of methyldopa according to the invention in its consistency of effect.

4. Tolerability: The tolerability of methylpoda according to the invention was excellent and no differences were observed between it and the other treatments.

5. Adverse Effects: The incidence of side effects with methyldopa according to the invention at the doses studied was low and was not different from that observed with the other treatments.

6. Efficacy—Physician's Assessment: The physician's assessment of efficacy indicated no differences between methyldopa according to the invention and the other standard antihypertivsive treatments. The results of clinical trial No. 5, a study designed to evaluate the efficacy and tolerability of methyldopa according to the invention over 8 weeks of treatment, indicated at the dose studied an optimal antihypertensive effect thereby in 55% of the patients, with another 25% showing a good efficacy and another 10% showing a moderate antihypertensive activity.

The combined results of the five clinical trials indicate that the methylpoda formulation according to the invention is an effective once daily form of methyldopa in the control of mild to moderate hypertension when compared with standard antihypertensive therapy, and that it shows an advantage in terms of a greater consistency of effect resulting in a more uniform dosing regimen with fewer treatment failures.

What I claim is:

1. A controlled absorption methyldopa formulation for oral administration, comprising a pellet having a core of methyldopa or a pharmaceutically acceptable salt thereof in association with an organic acid, and a multi-layer membrane surrounding said core and containing a major proportion of a pharmaceutically acceptable film forming, water-insoluble polymer and a minor proportion of a pharmaceutically acceptable film forming, water-soluble polymer, the number of layers in said membrane and the ratio of said water-soluble polymer to said water-insoluble polymer being effective to permit release of said methyldopa from said pellet at a rate allowing controlled absorption thereof over a twenty four hour period following oral administration said rate being measured in vitro as a dissolution rate which is substantially pH independent and which when measured in a Basket Assembly according to U.S. Pharmacopoeia XX at 37° C. and 75 r.p.m., substantially corresponds to the following dissolution pattern:
    (a) from 25 to 50% of the total methyldopa is released after 1 hour of measurement in said assembly;
    (b) from 50 to 80% of the total methyldopa is released after 3 hours of measurement in said assembly;
    (c) from 80 to 100% of the total methyldopa is released after 5 hours of measurement in said assembly; and
    (d) from 90 to 100% of the total methyldopa is released after 7 hours of measurement in said assembly.

2. A formulation according to claim 1, wherein the organic acid is selected from the group consisting of one or more of the following acids: adipic acid, citric acid, fumaric acid, malic acid, succinic acid and tartaric acid, the methyldopa and organic acid being present in a ratio of from 1:1 to 10:1.

3. A formulation according to claim 2, wherein the core includes one or more additional components selected from the group consisting of a lubricant, a dispersing agent and a surfactant.

4. A formulation according to claim 2, wherein the core comprises:
    (a) a powder mixture comprising methyldopa or a pharmaceutically acceptable salt thereof and at least one organic acid selected from the group consisting of adipic acid, citric acid, fumaric acid, malic acid, succinic acid and tartaric acid, and
    (b) a polymeric material comprising a major proportion of a pharmaceutically acceptable water-soluble polymer and a minor proportion of a pharmaceutically acceptable water-insoluble polymer, said core comprising layers of said powder mixture and said polymeric material superimposed one upon the other wherein said polymeric material is present in an amount sufficient to ensure that all of said powder mixture is coated into said core.

5. A formulation according to claim 4, wherein the pharmaceutically acceptable water-soluble polymer is selected from the group consisting of hydroxpropylmethylcellulose and polyvinylpyrrolidone.

6. A formulation according to claim 4, wherein the pharmaceutically acceptable water-soluble polymer is selected from the group consisting of methylcellulose, ethylcellulose, propylcellulose and shellac.

7. A formulation according to claim 4, wherein the polymeric material of the core compriseds a major proportion of a copolymer of acrylic and methacrylic acid esters which is freely permeable to water and a minor proportion of a copolymer of acrylic and methacrylic acid esters which is slightly permeable to water.

8. A formulation according to claim 1, wherein the multi-layer membrane has a major proportion of a pharmaceutically acceptable film-forming, water insoluble polymer and a minor proportion of a pharmaceutically acceptable film-forming water soluble polymer, the ratio of water insoluble to water soluble polymer being determined by the inherent solubility characteristics of the respective polymers and said membrane being built up by applying a plurality of coats of membrane polymer solution to the core.

9. A formulation according to claim 8, wherein the pharmaceutically acceptable film-forming water insoluble polymer of the membrane is selected from the group consisting of shellac and ethylcellulose and the pharmaceutically acceptable film-forming water soluble polymer is selected from the group consisting of polyvinylpyrrolidone and hydroxypropylcellulose.

10. A formulation according to claim 1, wherein the multi-layer membrane consists of a film forming copolymer of acrylic and methacrylic acid esters which is slightly permeable to water and a film-forming copolymer of acrylic and methacrylic acid esters which is freely permeable to water.

11. A capsule comprising pellets according to claim 1.

* * * * *